United States Patent
Hoehse et al.

(10) Patent No.: US 10,274,419 B2
(45) Date of Patent: Apr. 30, 2019

(54) CONTAINER HAVING A MEASURING CELL

(71) Applicant: Sartorius Stedim Biotech GmbH, Goettingen (DE)

(72) Inventors: Marek Hoehse, Goettingen (DE); Christian Grimm, Heiligenstadt (DE)

(73) Assignee: Sartorius Stedim Biotech GmbH (DE)

( * ) Notice: Subject to any disclaimer, the term of this patent is extended or adjusted under 35 U.S.C. 154(b) by 0 days.

(21) Appl. No.: 16/061,719

(22) PCT Filed: Dec. 22, 2016

(86) PCT No.: PCT/EP2016/082436
§ 371 (c)(1),
(2) Date: Jun. 13, 2018

(87) PCT Pub. No.: WO2017/109104
PCT Pub. Date: Jun. 29, 2017

(65) Prior Publication Data
US 2018/0372617 A1    Dec. 27, 2018

(30) Foreign Application Priority Data
Dec. 23, 2015  (DE) .......................... 10 2015 122 745

(51) Int. Cl.
G01N 21/03   (2006.01)
C12M 1/00   (2006.01)
C12M 1/34   (2006.01)

(52) U.S. Cl.
CPC ......... *G01N 21/0303* (2013.01); *C12M 23/28* (2013.01); *C12M 41/36* (2013.01);
(Continued)

(58) Field of Classification Search
CPC ............. G01N 35/0098; G01N 35/026; G01N 35/1011; G01N 2021/399;
(Continued)

(56) References Cited

U.S. PATENT DOCUMENTS

2004/0144163 A1* 7/2004 Kram ...................... G01M 3/38
73/40.7
2008/0032389 A1  2/2008  Selker et al.
(Continued)

FOREIGN PATENT DOCUMENTS

DE   10 2008 036 934   2/2010
DE   10 2010 007 559   8/2011
DE   10 2011 101 107   11/2012

OTHER PUBLICATIONS

International Search Report dated Apr. 18, 2017.
(Continued)

*Primary Examiner* — Michael P Stafira
(74) *Attorney, Agent, or Firm* — Gerald E. Hespos; Michael J. Porco; Matthew T. Hespos

(57) ABSTRACT

A container (1) has a measuring-cell housing (5) that protrudes into the container interior (2). The measuring-cell housing (5) has a measuring gap (6) bounded by two opposed spaced-apart lateral surfaces (8, 9), and a connecting surface (10) connects the lateral surfaces (8, 9). Each lateral surface (8, 9) has an optical window (11, 12). A first optical fiber (15, 15') is arranged before the first window (11) and a second optical fiber (17, 17') is arranged before the second window (12). Receiving channels (14, 16, 18) are arranged before the windows (11, 12, 13) and subsequently can be fit with the optical fibers (15, 15', 17, 17', 19) from the outside. The measuring-cell housing (5) having the windows (11, 12, 13) and the receiving channels (14, 16, 18) is connected fixedly to the wall (3) of the container interior (2).

14 Claims, 6 Drawing Sheets

(52) U.S. Cl.
CPC ............ *G01N 2021/0321* (2013.01); *G01N 2201/0245* (2013.01)

(58) Field of Classification Search
CPC .......... G01N 2035/00534; G01N 2035/00891; G01N 2035/009; G01N 2035/0091; G01N 21/1717; G01N 21/3504; G01N 21/359; G01N 21/39; G01N 21/4788; G01N 21/553; G01N 21/554; G01N 21/65; G01N 21/718; G01N 21/90; G01N 33/5038; G01N 33/5088; G01N 33/5091; G01N 35/00623; G01N 35/00722; G01N 35/1016; G01B 11/02; G01B 11/14; G01B 21/16; G01B 7/02; G01B 7/12; G02B 21/002; G02B 21/06; G02B 21/18; G02B 21/245; G02B 21/36; G02B 27/62
See application file for complete search history.

(56) References Cited

U.S. PATENT DOCUMENTS

| | | | |
|---|---|---|---|
| 2009/0075248 A1* | 3/2009 | Debreczeny | G01N 15/06 435/3 |
| 2010/0035337 A1 | 2/2010 | Bahnemann et al. | |
| 2013/0039810 A1 | 2/2013 | Riechers | |
| 2014/0054186 A1 | 2/2014 | Riechers et al. | |
| 2015/0330903 A1 | 11/2015 | Koerperick et al. | |

OTHER PUBLICATIONS

Translation of International Preliminary Report on Patentability for International Application No. PCT/EP2016/082436 dated Jun. 26, 2018.

* cited by examiner

CONTAINER HAVING A MEASURING CELL

BACKGROUND

Field of the Invention

The invention relates to a container having a measuring-cell housing of an optical measuring cell that protrudes into the container interior of the container, wherein the measuring-cell housing has a measuring gap, which is bounded by two opposite-facing lateral surfaces spaced apart from each other and by a connecting surface that connects the lateral surfaces, wherein the lateral surfaces each have an optical window, and wherein at least one first optical fiber can be arranged before the first window and at least one second optical fiber can be arranged before the second window.

Description of the Related Art

DE 10 2008 036 934 B4 discloses a bioreactor (container) having a measuring-cell housing of an optical measuring cell that protrudes into the container interior of the container. The measuring-cell housing is designed as part of a transmission probe that protrudes with its free end into the container interior of the bioreactor and has a first optical window as well as a second optical window arranged at a distance therefrom that delimit a cuvette gap or measuring gap that is filled by the sample volume of the container interior. A first optical fiber is arranged before the first window and a second optical fiber is arranged before the second window.

The known bioreactor (container) has the disadvantage that the first optical window is formed by a partial region of a deflecting prism, which is relatively elaborate and cost-intensive—especially for single-use bioreactors.

For sterilization reasons, in single-use bioreactors the optical measuring cell is welded in place and jointly sterilized. Different measuring cells must therefore be developed, qualified, validated and welded in place for different types of spectroscopy.

The present invention therefore seeks to provide a container, in particular for use as a single-use bioreactor, having an inexpensive optical measuring cell suitable for different types of spectroscopy.

SUMMARY

The invention relates to a container, such as a bioreactor, having a measuring-cell housing of an optical measuring cell that protrudes into the container interior of the container. The measuring-cell housing has a measuring gap that is bounded by two opposite-facing lateral surfaces spaced apart from each other at a distance and by a connecting surface that connects the lateral surfaces. Each lateral surface has an optical window. At least one first optical fiber can be arranged before the first window and at least one second optical fiber can be arranged before the second window. The measuring-cell housing has receiving channels arranged before the windows for receiving the at least one optical fiber in each case. The optical fibers subsequently can be fit into the receiving channels from the outside, and the measuring-cell housing having the windows and the receiving channels is connected fixedly to the wall of the container interior.

The receiving channels subsequently can be fit with the optical fibers, based on the chosen type of spectroscopy. Thus, the measuring-cell housing can be built inexpensively into the container and can be used universally for optical measuring cells for different types of spectroscopy.

The modular structure enables various optical combinations without any need to change the basic structure. Furthermore, the optical structure of the multifunctional (single-use) measuring cell makes it possible to minimize optical components in the single-use part, with a corresponding reduction of costs. In contrast to known sensor heads, the fibers are light conductors and are not integrated permanently into the probe but rather the fibers can be inserted reversibly into the single-use part of the optical measuring cell via the receiving channels, as required, depending on the type of spectroscopy.

Ends of the receiving channels facing toward the windows may be oriented orthogonally to the windows. Orthogonal orientation of the fiber ends following insertion of the fibers is ensured, for example, by a corresponding curvature in the receiving channels. Thus, a deflecting prism or deflecting mirror can therefore be dispensed with.

The connecting surface of the measuring-cell housing may have a third optical window, with a third receiving channel being arranged before the third optical window. At least one third optical fiber subsequently can be fit in the third receiving channel from the outside. The third window enables light to be directed from the measuring gap to the third optical fiber at an angle of 90°, for example, relative to the first and second fibers. The light can then be directed to a detector via the third fiber.

A multi-lens optical imaging device (such as found in a microscope) can also be inserted into the third receiving channel. In this case, too, the single-use part is only the third window or a final lens; all other optical elements can be inserted reversibly into and removed from the third receiving channel. This multi-lens optical device can, for example, be used for Raman spectroscopy as well as for dark-field microscopy.

The two other receiving channels do not necessarily also have to be used, but rather can remain blind. A removable third window also enables the third receiving channel to be used for taking samples. This makes it possible to ensure that the sample taken is virtually identical to the sample quantity that was just measured. As a result, inhomogeneities in the container interior cannot affect the samples removed for calibration. Therefore, the third receiving channel optionally can be used for taking samples, detecting a 90° scatter or inserting a multi-lens optical device.

Ends of the receiving channels facing away from the windows may have receiving openings with longitudinal axes that extend parallel to one another. The parallel arrangement of the longitudinal axes enables the fibers to be connected to the measuring-cell housing by means of corresponding plug-in, snap-lock or screw connections. In particular, the parallel longitudinal axes make it possible also to use a common plug-in connection.

The receiving channels of the measuring-cell housing may form a common spatial depression in which the optical fibers are arranged fixedly before the windows by means of brackets. This arrangement enables a rapid and precise orientation of the optical fibers. Brackets also enable the optical fibers to be fixed in the spatial depression such that they are arranged before the windows.

The measuring-cell housing, along with windows and receiving channels may form a single-use part of the optical measuring cell while the optical fibers, along with connected light sources and/or sensors and evaluation and control electronics, form a reusable part of the optical measuring cell.

The optical windows may be lenses, filters or diffusely reflecting surfaces.

For transmission purposes, light from a light source can be conducted via the at least one first fiber in the first receiving channel, through the first window into the measuring gap with a sample volume, and further via the second window and the at least one second fiber arranged in the second receiving channel, to a detector. At least one pinhole aperture can be arranged between the second window or lens and the second fiber arranged in the second receiving channel. The end of the second fiber facing the pinhole aperture can be arranged at a distance from the pinhole aperture. This arrangement makes it possible to use the device to perform, relatively easily and inexpensively, an evaluation via spectroscopic transmission.

For reflection purposes, light from a light source can be conducted via a first fiber in the first receiving channel, through the first window into the measuring gap with a sample volume and, as light that has been reflected or scattered by the sample volume, the light can be conducted back via the first window and a second fiber arranged in the first receiving channel, to a detector. In principle, fiber bundles can also be used instead of fibers. The detection, at least, can be done via fiber bundles (e.g. annularly arranged around the excitation fiber) especially for reflection measurement. This arrangement therefore makes it possible to use the device to perform, relatively easily and inexpensively, an evaluation by means of spectroscopic reflection.

For transflexion purposes light from a light source can be conducted via a first fiber in the first receiving channel, through the first window into the measuring gap with a sample volume, and further via the second window in the second receiving channel onto a diffusely reflecting surface, and the light can be conducted as reflected light back via the first window and a second fiber arranged in the first receiving channel to a detector. The reflecting surface can be arranged at the free end of a dummy fiber (or, e.g. a tubular element) inserted into the second receiving channel. In principle, the second window can also be designed as a reflector. This arrangement therefore makes it possible to use the device to perform, relatively easily and inexpensively, an evaluation by means of spectroscopic transflection.

Light scattered by the sample volume, i.e. light after it has interacted with the sample, can be conducted via the third optical window and the third optical fiber arranged in the third receiving channel, to a detector.

The container may be a single-use bioreactor or a single-use mixing bag.

Additional features and advantages of the invention are evident from the following special description and the drawings.

DETAILED DESCRIPTION

Figure 1:
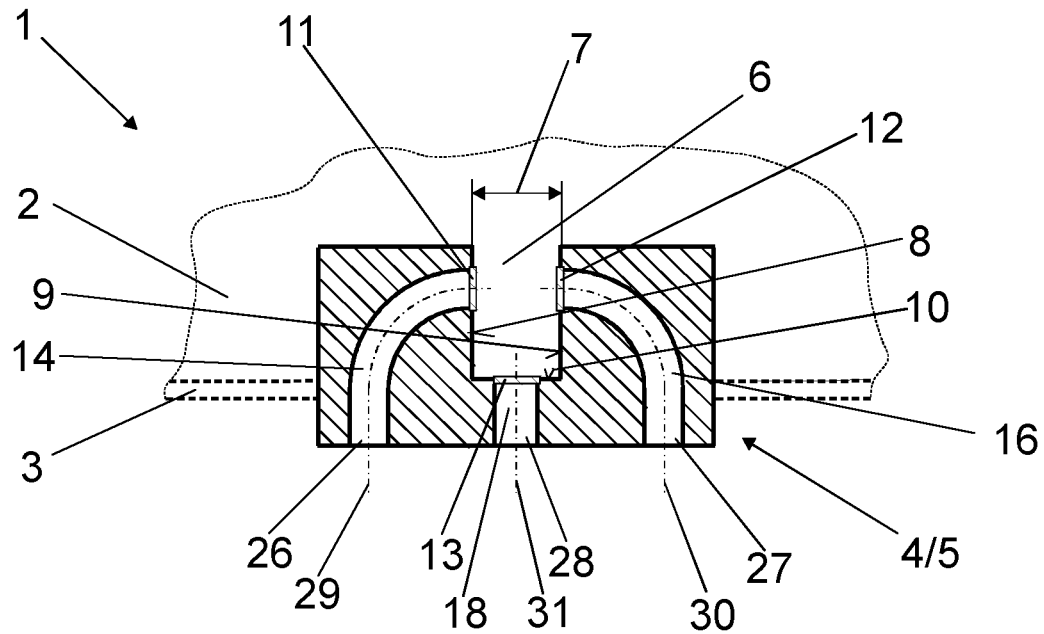
FIG. 1 is a cross-sectional lateral and detail view of a container depicted with dotted lines (single-use bioreactor) having a measuring-cell housing with receiving channels and optical windows.

A container 1, for example, a single-use bioreactor, essentially comprises a container interior 2, a wall 3 and an optical measuring cell 4.

The container interior 2 is enclosed by the wall 3. The measuring cell 4 has a measuring-cell housing 5 that protrudes through the wall 3, to which it is fixedly connected, into the container interior 2. On the inner side of the container, the measuring-cell housing 5 has a "U"-shaped cut-out measuring gap 6 to receive a sample volume for analysis. The measuring gap 6 is bordered by two lateral surfaces 8, 9 facing one another at a distance 7, and by a connecting surface 10 that connects the lateral surfaces 8, 9. The first lateral surface 8 has a first optical window 11, the second lateral surface 9 has a second optical window (12) and the connecting surface 10 has a third optical window 13.

On its side facing away from the measuring gap 6, the measuring-cell housing 5 has a first receiving channel 14 arranged before the first window 11 in order to receive at least one first optical fiber 15. In corresponding fashion, on its side facing away from the measuring gap 6, the measuring-cell housing 5 has a second receiving channel 16 arranged before the second window 12 in order to receive at least one second optical fiber 17. Furthermore, on its side facing away from the measuring gap 6, the measuring-cell housing 5 has a third receiving channel 18 arranged before the third window 13 in order to receive at least one third optical fiber 19.

At their ends facing away from the windows 11, 12, 13, the receiving channels 14, 16, 18 have receiving openings 26, 27, 28, the longitudinal axes 29, 30, 31 of which extend parallel to one another.

Figure 2:
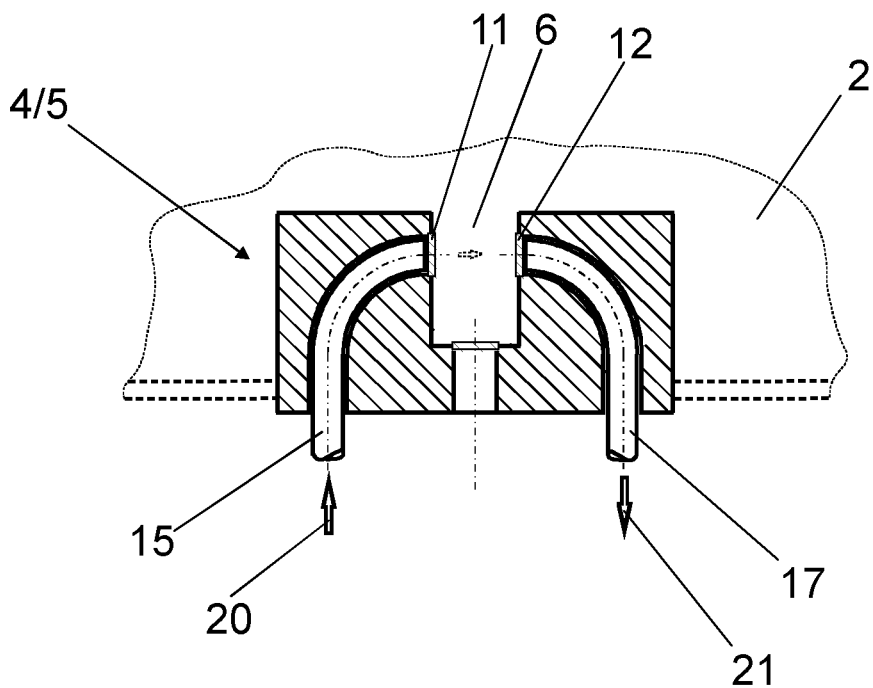
FIG. 2 is a cross-sectional view of the measuring-cell housing from FIG. 1 with a first fiber in the first receiving channel and a second fiber in the second receiving channel.

According to the exemplary embodiment from FIG. 2, for the purpose of spectroscopic transmission, light from a light source (not shown) can be conducted via the first optical fiber 15 in the first receiving channel 14, through the first window 11 into the measuring gap 6 with the sample volume, and further via the second window 12 and the second fiber 17 arranged in the second receiving channel 16 the light can be conducted as transmitted light 21 to a detector (not shown). At least one pinhole aperture (not shown) can be arranged between the second window 12 and the second fiber 17 arranged in the second receiving channel 16.

Figure 3:
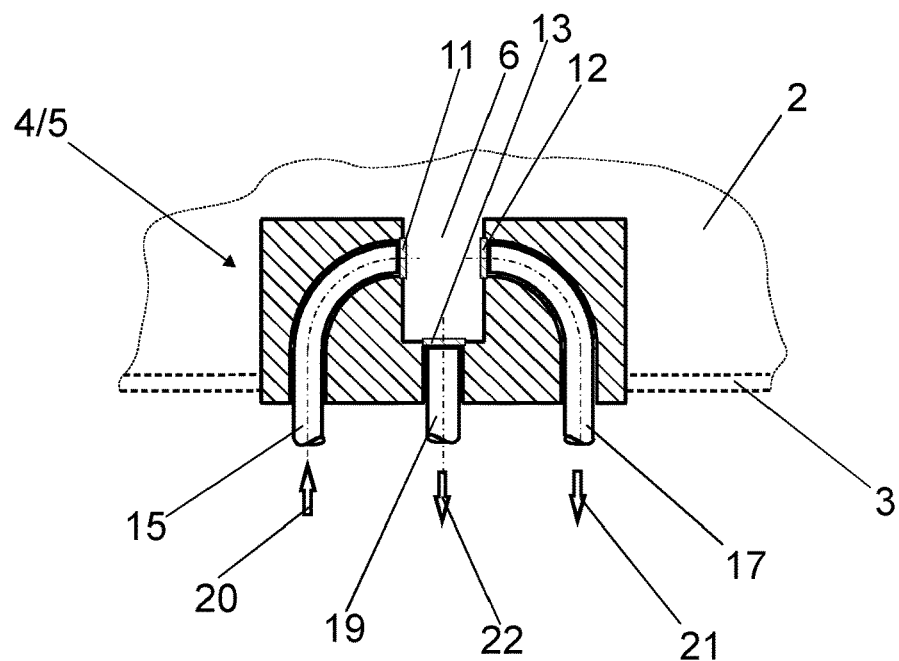
FIG. 3 is a cross-sectional view of the measuring-cell housing from FIG. 1 with a first fiber in the first receiving channel, a second fiber in the second receiving channel and a third fiber in the third receiving channel.

According to the exemplary embodiment from FIG. 3, reflected light 22 from the sample volume can additionally be conducted via the third optical window 13 and the third optical fiber 19 arranged in the third receiving channel 18, to a detector (not shown).

Figure 4:
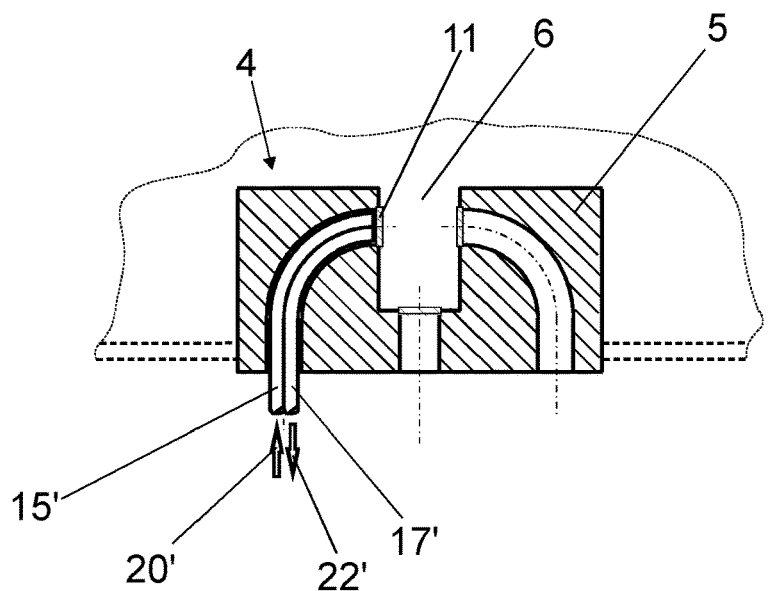
FIG. 4 is a cross-sectional view of the measuring-cell housing from FIG. 1 with a first fiber and a second fiber in the first receiving channel.

According to the exemplary embodiment from FIG. 4, for reflection purposes light from a light source 20' can be conducted via a first optical fiber 15' in the first receiving channel 14, through the first window 11 into the measuring gap 6 with the sample volume, and it can be conducted back as reflected light 22' from the sample volume, via the first window 11 and a second fiber 17' arranged in the first receiving channel 14, to a detector.

Figure 5:
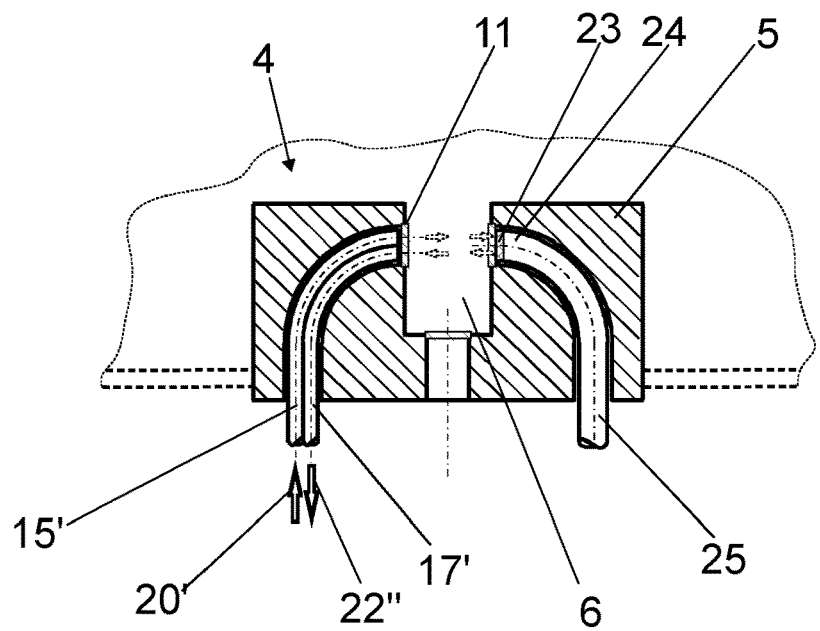
FIG. 5 is a cross-sectional view of the measuring-cell housing from FIG. 1 with a first fiber and a second fiber in the first receiving channel and with a dummy fibre with a diffusely reflecting surface in the second receiving channel.
Figure 6:
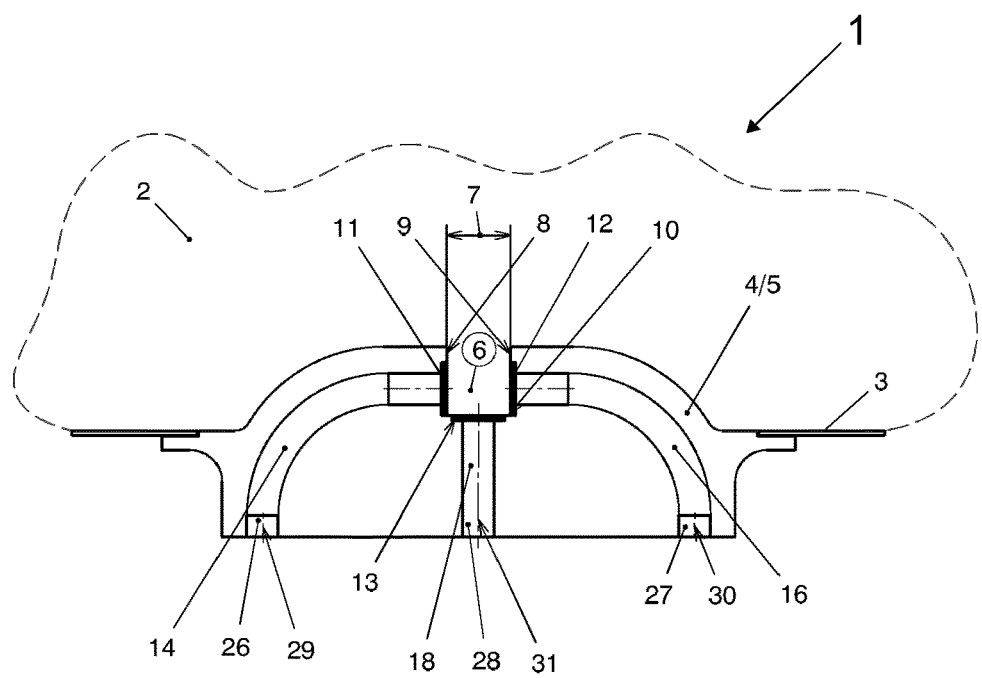
FIG. 6 is a cross-sectional lateral and detail view of an additional container (single-use bioreactor) depicted with dotted lines having a measuring cell housing with receiving channels and optical windows.
Figure 7:
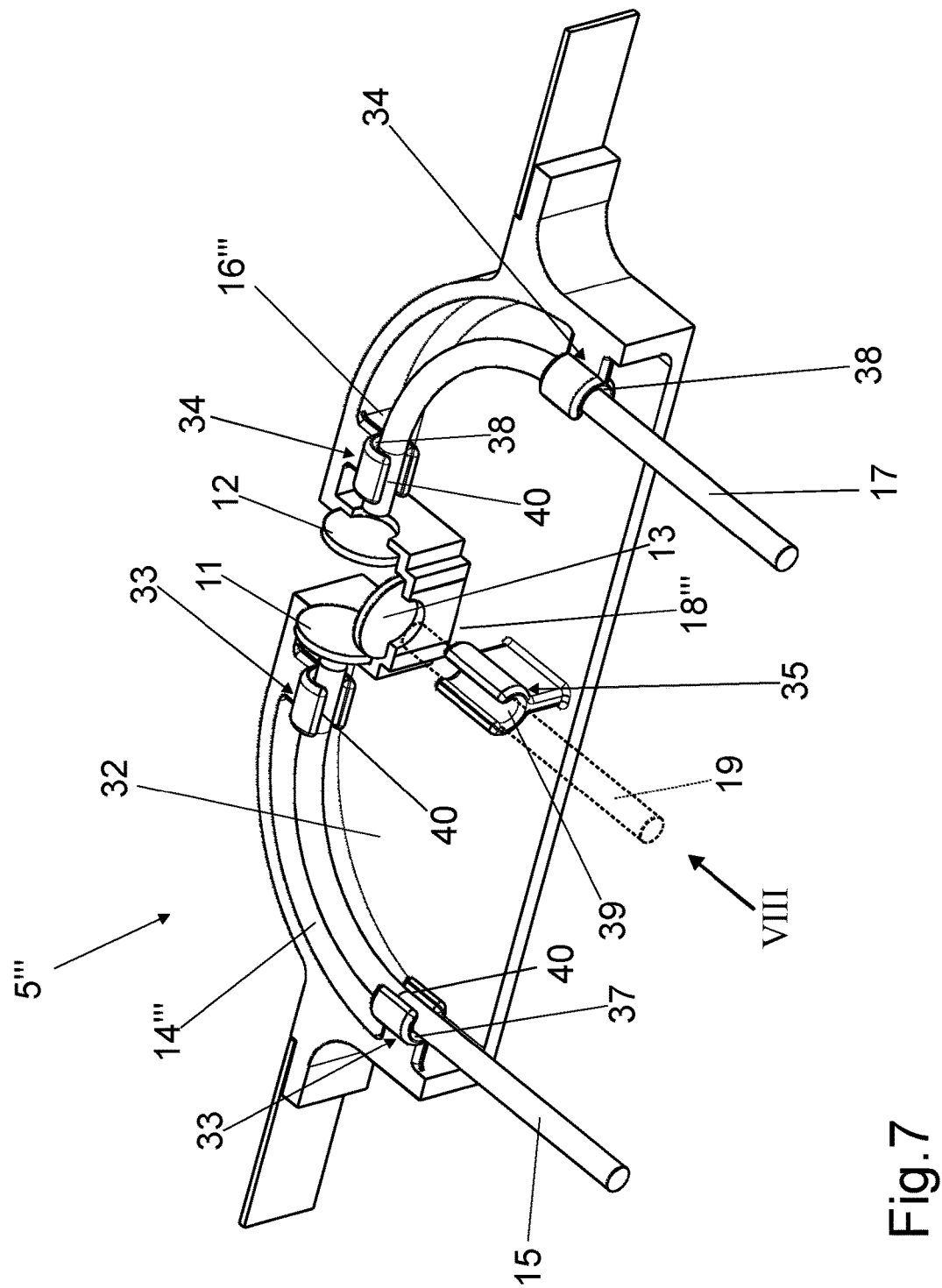
FIG. 7 is a three-dimensional perspective representation of an additional measuring-cell housing, the receiving channels of which are combined to form a common depression.
Figure 8:
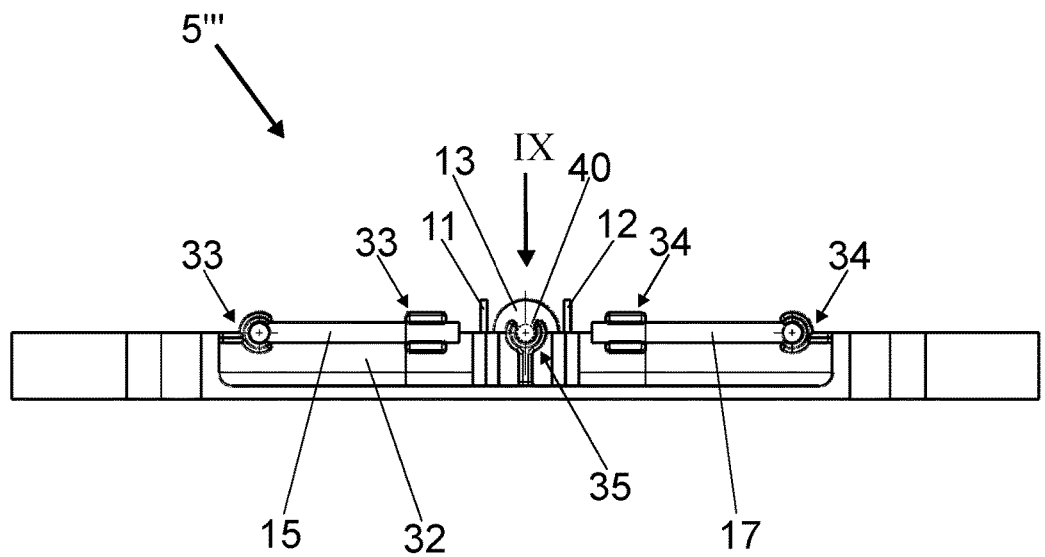
FIG. 8 is a lateral view of the measuring housing from FIG. 7 from Direction VIII.
Figure 9:
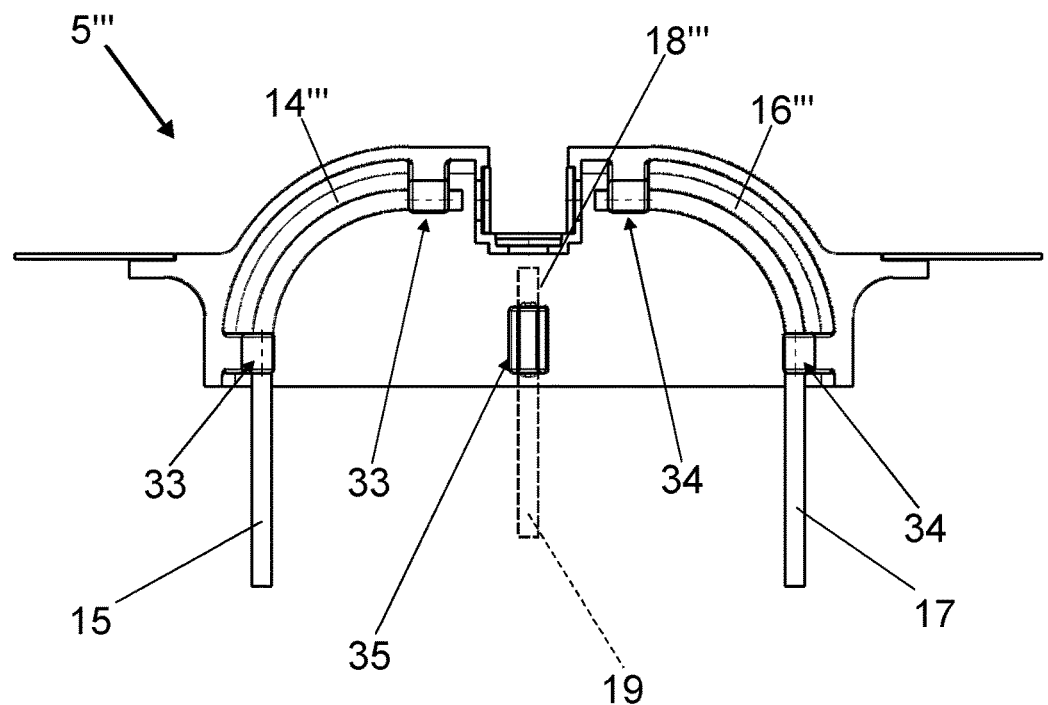
FIG. 9 is a top plan view of the measuring housing from FIG. 8 from Direction IX.

According to the exemplary embodiment from FIG. 5, for transflexion purposes light from a light source 20' can be conducted via the first fiber 15' in the first receiving channel 14, through the first window 11 into the measuring gap 6 with the sample volume, and further via the second window 12 in the second receiving channel 16, onto a diffusely reflecting surface 23, and it is conducted back as reflected light 22" via the first window 11 and a second fiber 17' arranged in the first receiving channel 14, to a detector. The reflecting surface 23 can be arranged at the free end of a dummy fiber 25 inserted into the second receiving channel.

According to the exemplary embodiment from FIGS. 7 to 10, the receiving channels 14''', 16''', 18''' of the measuring cell 5''' form a spatial depression 32 in which they merge into each other. The optical fibers 15, 17, 19 are fixed in the depression 32 by means of brackets 33, 34, 35 of the receiving channels 14''', 16''', 18''' associated with the depression 32. Possible types of brackets 33, 34, 35 include: click closures, bayonet closures and screw closures. The optical fibers 15, 17, 19 are fixed in the brackets 33, 34, 35 such that, with their free ends, they are arranged before the windows 11, 12, 13 on the outside thereof. The brackets 33, 34, 35 each have a receiving channel piece 37, 38, 39, the receiving cross-section of each of which forms a channel segment to receive the associated optical fibers 15, 17, 19. The receiving channel pieces 37, 38, 39 can each have a longitudinal slot 40 to facilitate fastening of the optical fibres 15, 17, 19.

Figure 10:
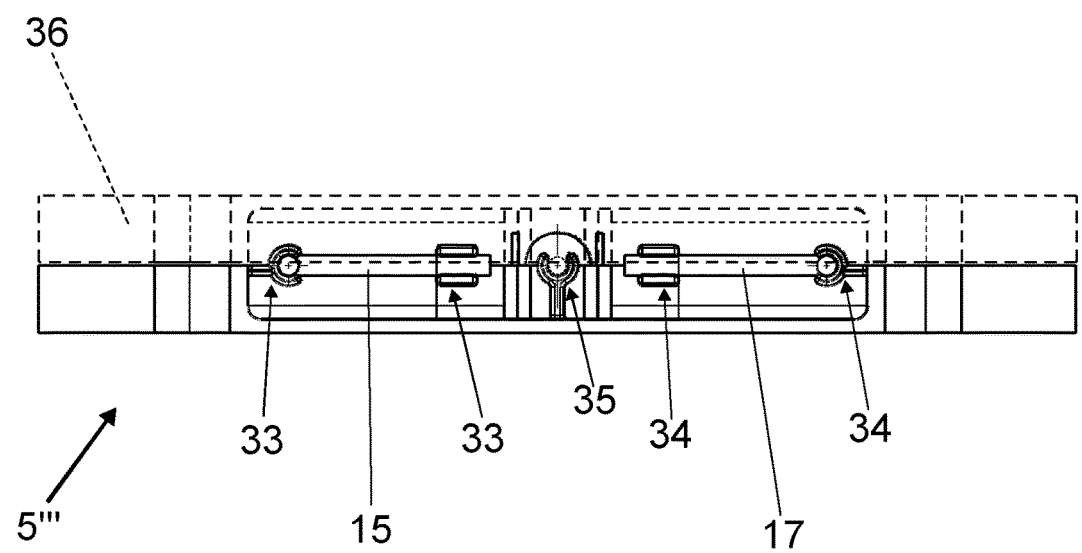
FIG. 10 is a lateral view of the measuring housing from FIG. 8 with a cover indicated with dotted lines.

According to the exemplary embodiment from FIG. 10, the depression 32 of the measuring cell 5''' is covered, at least in part, by a cover piece 36.

Of course, the embodiments discussed in the specific description and shown in the Figures are merely illustrative exemplary embodiments of the present invention. In the light of the present disclosure a person skilled in the art has a broad spectrum of optional variations available.

In particular, instead of the fibers 15, 15', 17, 17', 18, 19, a fiber bundle (also not shown) can be used. In this case, the fibers 15, 15', 17, 17', 18, 19 or the fiber bundles can be inserted directly into the receiving channels 14, 16, 18 before use.

The fibers 15, 15', 17, 17', 18, 19 or the fiber bundles can be connected to the measuring-cell housing 5 by means of screws, clamps or other fasteners (not shown). This enables reproducible positioning of the fibers 15, 15', 17, 17', 18, 19 or the fiber bundles.

LIST OF REFERENCE NUMBERS

1 Container
2 Container interior
3 Wall of 1
4 Measuring cell
5, 5''' Measuring-cell housing of 4
6 Measuring gap of 5
7 Distance
8 First lateral surface
9 Second lateral surface
10 Connecting surface
11 First window of 8
12 Second window of 9
13 Third window of 10
14, 14''' First receiving channel
15, 15' First fiber
16, 16''' Second receiving channel
17, 17' Second fiber
18, 18''' Third receiving channel
19 Third fiber
20, 20' Light
21 Transmitted light
22, 22', 22" Reflected light
23 Diffusely reflecting surface
24 Free end of 25
25 Dummy fiber
26 Receiving opening
27 Receiving opening
28 Receiving opening
29 Longitudinal axis
30 Longitudinal axis
31 Longitudinal axis
32 Depression of 5'''
33 Bracket of 14'''
34 Bracket of 16'''
35 Bracket of 18'''
36 Cover piece
37 Channel piece of 33
38 Channel piece of 34
39 Channel piece of 35
40 Longitudinal slot of 37, 38, 39

The invention claimed is:

1. A container (1) having a measuring-cell housing (5) of an optical measuring cell (4) that protrudes into the container interior (2) of the container, wherein the measuring-cell housing (5) has a measuring gap (6), which is bounded by two opposite-facing lateral surfaces (8, 9) spaced apart from each other at a distance (7) and by a connecting surface (10) that connects the lateral surfaces (8, 9), wherein the lateral surfaces (8, 9) each have an optical window (11, 12), and wherein at least one first optical fiber (15, 15') can be arranged before the first window (11) and at least one second optical fiber (17, 17') can be arranged before the second window (12),
wherein
the measuring-cell housing (5) has receiving channels (14, 16, 18) arranged before the windows (11, 12, 13) for receiving the at least one optical fiber (15, 15', 17, 17', 19) in each case,
the receiving channels (14, 16, 18) can be subsequently fitted from the outside with the optical fibers (15, 15', 17, 17', 19), and
the measuring-cell housing (5) having the windows (11, 12, 13) and the receiving channels (14, 16, 18) is fixedly connected to the wall (3) of the container interior (2).

2. The container of claim 1,
wherein
at their ends facing the windows (11, 12, 13), the receiving channels (14, 14''', 16, 16''', 18, 18''') are oriented orthogonally to the windows (11, 12, 13).

3. The container of claim 1,
wherein
the measuring-cell housing (5) has a third optical window (13) on its connecting surface (10) and
that before the third optical window (13) there is arranged a third receiving channel (18) that can be fitted from the outside with at least one third optical fiber (19).

4. The container of claim 1,
wherein
at their ends facing away from the windows (11, 12, 13), the receiving channels (14, 14''', 16, 16''', 18, 18''') have receiving openings (26, 27, 28) the longitudinal axes (29, 30, 31) of which extend parallel to one another.

5. The container of claim 1,
wherein
the measuring-cell housing (5) having windows (11, 12, 13) and receiving channels (14, 16, 18) constitutes a single-use part of the optical measuring cell (4) and
that the optical fibers (15, 15', 17, 17', 19), along with connected light sources and/or sensors and evaluation and control electronics, constitute a reusable part of the optical measuring cell (4).

6. The container of claim 1,
wherein
the optical windows (11, 12, 13) are lenses.

7. The container of claim 1,
wherein
for transmission purposes light 20 from a light source can be conducted via the at least one first fiber (15) in the first receiving channel (14, 14'''), through the first window (11) into the measuring gap (6) with a sample volume, and further via the second window (12) and the at least one second fiber (17) arranged in the second receiving channel (16, 16'''), to a detector.

8. The container of claim 7,
wherein
at least one pinhole aperture is arranged between the second window (12) and the second fiber (17) arranged in the second receiving channel (16).

9. The container of claim 1,
wherein
for reflection purposes, light 20' from a light source can be conducted via a first fiber (15') in the first receiving channel (14), through the first window (11) into the measuring gap (6) with a sample volume, and can be conducted back as reflected light (22') from the sample volume via the first window (11) and a second fiber (17') arranged in the first receiving channel (14), to a detector.

10. The container of claim 1,
wherein
for transflection purposes, light 20' from a light source can be conducted via a first fiber (15') in the first receiving channel (14), through the first window (11) into the measuring gap (6) with a sample volume, and be further conducted via the second window (12) in the second receiving channel (16) onto a diffusely reflecting surface (23), and be conducted back as reflected light (22''), via the first window (11) and a second fiber (17') arranged in the first receiving channel (14), to a detector.

11. The container of claim 10,
wherein
the reflecting surface (23) is arranged at the free end of a dummy fiber (26) inserted into the second receiving channel (16).

12. The container of claim 3,
wherein
scattered light (22) from a sample volume can be conducted via the third optical window (13) and the third optical fiber (19) arranged in the third receiving channel (18, 18'''), to a detector.

13. The container of claim 1,
wherein
the container (1) is a single-use bioreactor or a single-use mixing bag.

14. The container of claim 1,
wherein
the receiving channels (14''', 16''', 18''') form a common spatial depression (32) in which the optical fibers (15, 17, 19) are fastened by means of brackets (33, 34, 35) and are arranged before the windows (11, 12, 13).

* * * * *